(12) United States Patent
Xu

(10) Patent No.: US 7,434,995 B2
(45) Date of Patent: Oct. 14, 2008

(54) X-RAY DETECTING APPARATUS AND X-RAY IMAGING APPARATUS

(75) Inventor: Jiake Xu, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 10 days.

(21) Appl. No.: 11/734,545

(22) Filed: Apr. 12, 2007

(65) Prior Publication Data
US 2007/0253538 A1   Nov. 1, 2007

(30) Foreign Application Priority Data
Apr. 13, 2006   (CN) .................. 2006 1 0073612

(51) Int. Cl.
H01J 31/49    (2006.01)
H05G 1/64     (2006.01)

(52) U.S. Cl. ..................... 378/189; 378/98.8

(58) Field of Classification Search ......... 378/189–197, 378/98.8
See application file for complete search history.

(56) References Cited

U.S. PATENT DOCUMENTS

| 4,024,403 A | 5/1977 | Bernstein et al. |
|---|---|---|
| 4,879,737 A | 11/1989 | Grady |
| 5,086,448 A | 2/1992 | Muthmann |
| 5,155,756 A | 10/1992 | Pare et al. |
| 5,416,824 A | 5/1995 | Goldhorn et al. |
| 6,349,793 B1 * | 2/2002 | Kincaid .................. 182/69.4 |
| 6,382,833 B2 | 5/2002 | Leandersson et al. |
| 7,062,011 B1 | 6/2006 | Tybinowski et al. |
| 2001/0036246 A1 * | 11/2001 | Graumann .................. 378/39 |
| 2004/0066891 A1 * | 4/2004 | Freytag et al. .............. 378/62 |
| 2004/0146142 A1 * | 7/2004 | Maijala .................... 378/102 |
| 2004/0159473 A1 * | 8/2004 | Vogel et al. ................ 180/9.1 |
| 2005/0100129 A1 * | 5/2005 | McKenna .................. 378/37 |
| 2006/0227938 A1 * | 10/2006 | Walker et al. .............. 378/195 |

FOREIGN PATENT DOCUMENTS

JP   10057360   3/1998

\* cited by examiner

Primary Examiner—Irakli Kiknadze
(74) Attorney, Agent, or Firm—Armstrong Teasdale LLP

(57) ABSTRACT

The present invention aims to provide an X-ray detecting apparatus having excellent stability of the support of an X-ray detector, and an X-ray imaging apparatus provided with this X-ray detecting apparatus. The X-ray imaging apparatus has an X-ray irradiating device and an X-ray detecting apparatus opposing to the X-ray irradiating device, wherein the X-ray detecting apparatus has a vertical first column; a second column that is telescopically engaged with the first column; a first raising/lowering mechanism that moves up/down the second column along the first column; a carriage attached to the second column; a second raising/lowering mechanism that moves up/down the carriage along the column; and an X-ray detector held by an arm extending horizontally from the carriage.

20 Claims, 6 Drawing Sheets

FIG. 6A
FIG. 6B
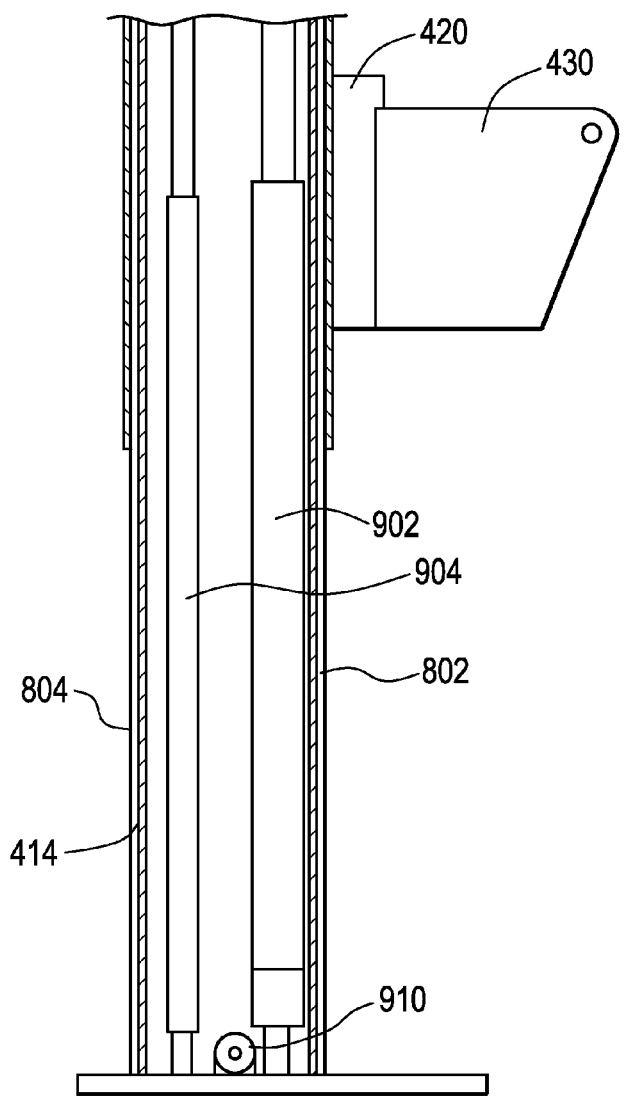
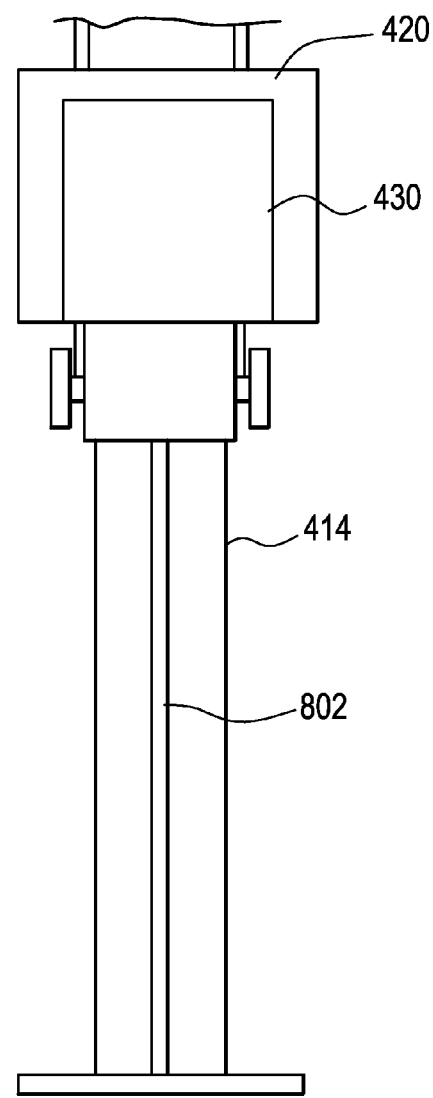

X-RAY DETECTING APPARATUS AND X-RAY IMAGING APPARATUS

CROSS REFERENCE TO RELATED APPLICATIONS

This application claims the benefit of Chinese Patent Application No. 200610073612.9 filed Apr. 13, 2006.

BACKGROUND OF THE INVENTION

The present invention relates to an X-ray detecting apparatus and an X-ray imaging apparatus, and more particularly to an X-ray detecting apparatus in which the height of an X-ray detector is variable, and to an X-ray imaging apparatus provided with this type of X-ray detecting apparatus.

There is an X-ray imaging apparatus in which the height of an X-ray detector can be changed in accordance with an X-ray source. In this type of X-ray imaging apparatus, an X-ray detector is supported by an extendable column standing upright from the floor, and X-ray is irradiated from an X-ray source hanging down from a ceiling (see Patent Reference 1, for example).

In order to support the X-ray detector with a cantilever method and to change the height thereof, the X-ray detecting apparatus is configured as shown in FIG. 7. Specifically, the X-ray detecting apparatus is configured as follows. A carriage 120 is attached to a column 110, which stands upright from the floor, so as to be capable of moving up and down. An arm 130 is horizontally disposed to the carriage 120. An X-ray detector 140 is attached to the leading end of the arm 130. On the other hand, an X-ray irradiating device is configured such that an X-ray source 320 is attached to an extendable column 310 hanging down from a ceiling.

[Patent Document 1] Japanese Published Unexamined Patent Application No. HEI10-057360

In the X-ray imaging apparatus having the above-mentioned configuration, the column 110 should be long enough to match with the elevating distance of the X-ray detector 140. In the case where the column 110 is so long as described above, the X-ray irradiating device should be installed such that the column 310 supporting the X-ray source 320 is sufficiently shifted ahead of the column 110 in order to avoid the interference with the column 110.

Therefore, the arm 130 supporting the X-ray detector 140 becomes long, so that the stability of the support of the X-ray detector 140 is deteriorated. Further, since both of the column 110 and the arm 130 are long, the X-ray detecting apparatus is made large-sized, which is inconvenient for packing, transportation, installation, or the like.

SUMMARY OF THE INVENTION

Therefore, an object of the present invention is to realize an X-ray detecting apparatus having excellent stability of the support of an X-ray detector, and an X-ray imaging apparatus provided with this X-ray detecting apparatus. The present invention further aims to realize an X-ray detecting apparatus convenient for packing, transportation, installation, or the like, and an X-ray imaging apparatus provided with this X-ray detecting apparatus.

In order to solve the above-mentioned subject, the invention in the first aspect is an X-ray detecting apparatus comprising: a vertical first column; a second column that is telescopically engaged with the first column; a first raising/lowering mechanism that moves up/down the second column along the first column; a carriage attached to the second column; a second raising/lowering mechanism that moves up/down the carriage along the column; and an X-ray detector held by an arm extending horizontally from the carriage.

In order to solve the above-mentioned subject, the invention in the second aspect is an X-ray imaging apparatus having an X-ray irradiating device and an X-ray detecting apparatus opposing to the X-ray irradiating device, wherein the X-ray detecting apparatus comprises: a vertical first column; a second column that is telescopically engaged with the first column; a first raising/lowering mechanism that moves up/down the second column along the first column; a carriage attached to the second column; a second raising/lowering mechanism that moves up/down the carriage along the column; and an X-ray detector held by an arm extending horizontally from the carriage.

It is preferable that the first column has a linear guide for the second column in terms of the prevention of meandering of the column in the upward and downward movements.

It is preferable that the first raising/lowering mechanism has a combination of a linear actuator and a gas spring in terms of easy extension of the column.

It is preferable that the second column has a linear guide for the second column in terms of the prevention of meandering of the column in the upward and downward movements.

It is preferable that the second raising/lowering mechanism has a combination of a gear and a chain in terms of easy extension of the column.

It is preferable that the first column has an encoder for detecting the absolute height of the X-ray detector in terms of the detection of the height of the X-ray detector.

EFFECT OF THE INVENTION

According to each aspect of the invention, an X-ray detecting apparatus comprises: a vertical first column; a second column that is telescopically engaged with the first column; a first raising/lowering mechanism that moves up/down the second column along the first column; a carriage attached to the second column; a second raising/lowering mechanism that moves up/down the carriage along the column; and an X-ray detector held by an arm extending horizontally from the carriage, whereby an X-ray detecting apparatus having excellent stability of the support of the X-ray detector and an X-ray imaging apparatus provided with this X-ray detecting apparatus can be realized. Further, an X-ray detecting apparatus convenient for packing, transportation, installation, or the like, and an X-ray imaging apparatus provided with this X-ray detecting apparatus can be realized.

Further objects and advantages of the present invention will be apparent from the following description of the preferred embodiments of the invention as illustrated in the accompanying drawings.

BRIEF DESCRIPTION OF THE DRAWINGS

FIGS. 6a and 6b are views showing a structure of a column extension mechanism in an X-ray detecting apparatus according to one example of a best mode for carrying out the present invention.

DETAILED DESCRIPTION OF THE INVENTION

Figure 1:
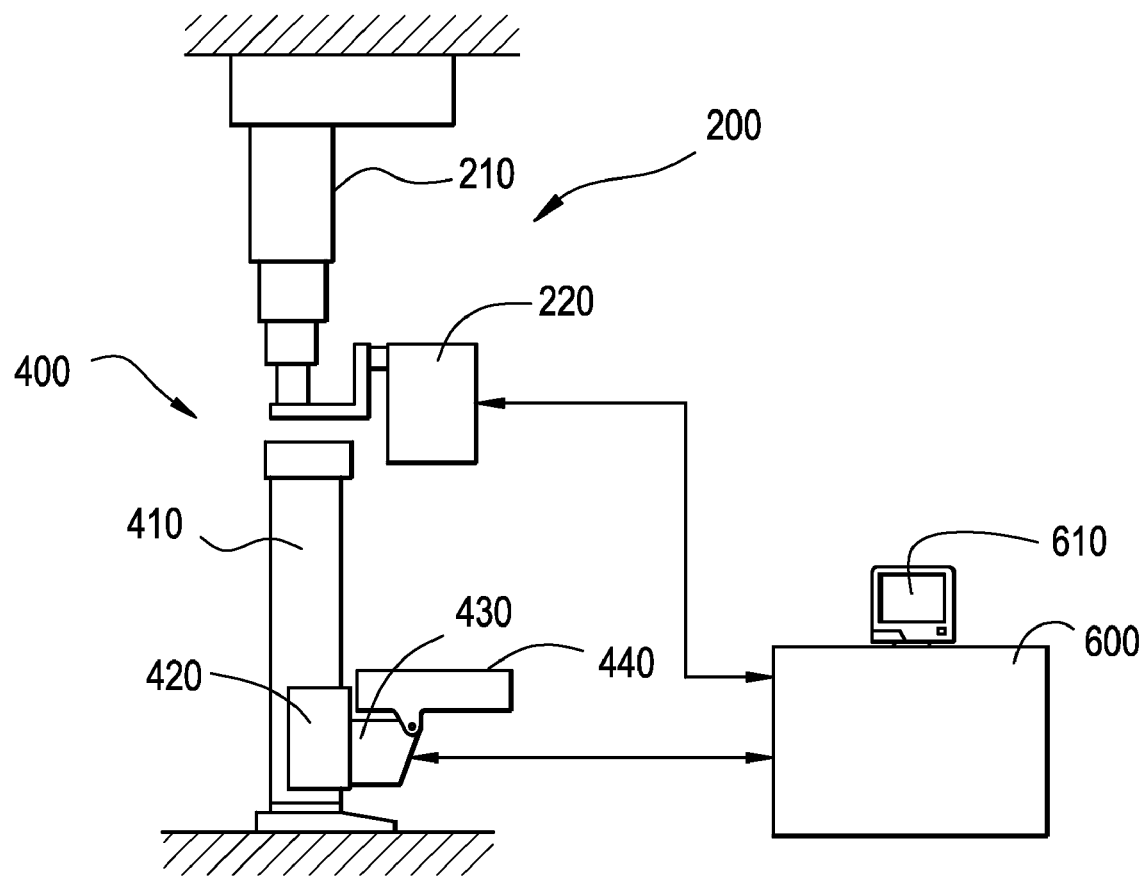
FIG. 1 is a view for showing a structure of an X-ray imaging apparatus according to one example of a best mode for carrying out the present invention.

A best mode for carrying out the invention will be explained hereinbelow in detail with reference to the drawings. It should be noted that the invention is not limited to the best mode for carrying out the invention. FIG. 1 shows a schematic construction of an X-ray imaging apparatus. This device is one example of the best mode for carrying out the invention. The construction of this device represents one example of the best mode for carrying out the invention relating to an X-ray imaging apparatus. Further, a part of the construction of this device represents one example of the best mode for carrying out the invention relating to an X-ray detecting apparatus.

As shown in FIG. 1, this device has an X-ray irradiating device 200 and an X-ray detecting apparatus 400. The X-ray irradiating device 200 is one example of an X-ray irradiating device according to the present invention. The X-ray detecting apparatus 400 is one example of an X-ray detecting apparatus according to the present invention.

The X-ray irradiating device 200 is configured such that an X-ray source 220 is attached at the leading end of a column 210 that hangs down from a ceiling. The X-ray source 220 changes its direction so as to be capable of changing the irradiating direction of X-ray. The column 210 supporting the X-ray source 220 is extendable in the longitudinal direction, and movable in the horizontal direction along the ceiling.

The X-ray detecting apparatus 400 is configured as follows. Specifically, a carriage 420 is disposed to a column 410 that stands upright from the floor so as to be capable of moving up and down. An arm 430 is horizontally attached to the carriage 420. An X-ray detector 440 is attached to the leading end of the arm 430. The X-ray detector 440 is a component having a flat-plate shape. It can change its inclination such that the light-receiving surface becomes horizontal or vertical in accordance with the incident direction of the X-ray.

The X-ray detector 440 is one example of an X-ray detector according to the present invention. The arm 430 is one example of an arm according to the present invention. The carriage 420 is one example of a carriage according to the present invention.

The detection signal of the X-ray detector 440 is inputted to an operator console 600. The operator console 600 reconstructs the radioscopic image of an object to be examined based upon the inputted signal, and displays the reconstructed radioscopic image on a display 610. Note that the X-ray detector 440 may be made of a photosensitive material which is photosensitive with X-ray. In this case, the radioscopic image is made visible by a developing process.

The operator console 600 controls the X-ray irradiating device 200 and the X-ray detecting apparatus 400 under the operation by an operator. As for the X-ray irradiating device 200, it controls the horizontal and vertical positions of the X-ray source 220 and the X-ray irradiating direction, and further, the X-ray intensity and irradiating timing. As for the X-ray detecting apparatus 400, it controls the height of the X-ray detector 440 depending upon the height of the X-ray source 220 and controls the inclination of the light-receiving surface so as to become horizontal or vertical depending upon the X-ray incident direction.

Figure 2A:
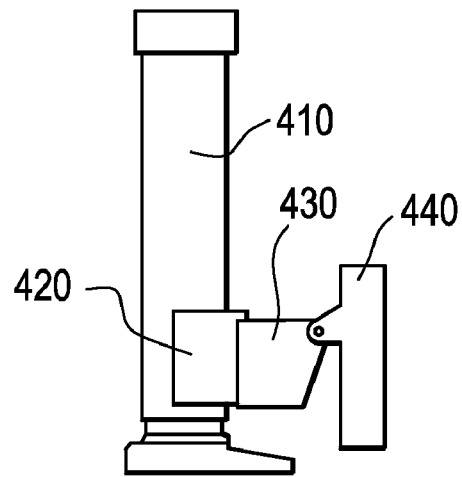
FIGS. 2a and 2b are views showing a structure of an X-ray detecting apparatus according to one example of a best mode for carrying out the present invention.
Figure 2B:
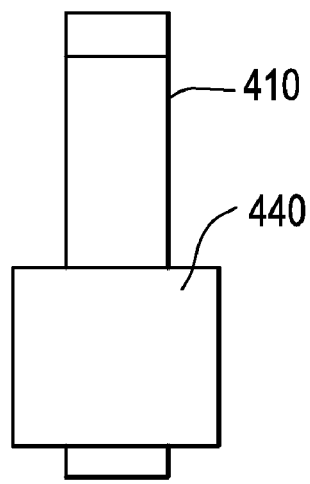
Figure 3A:
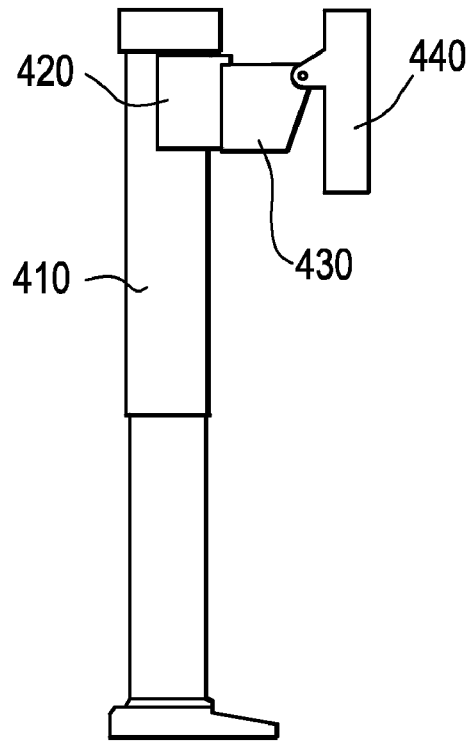
FIGS. 3a and 3b are views showing a structure of an X-ray detecting apparatus according to one example of a best mode for carrying out the present invention.
Figure 3B:
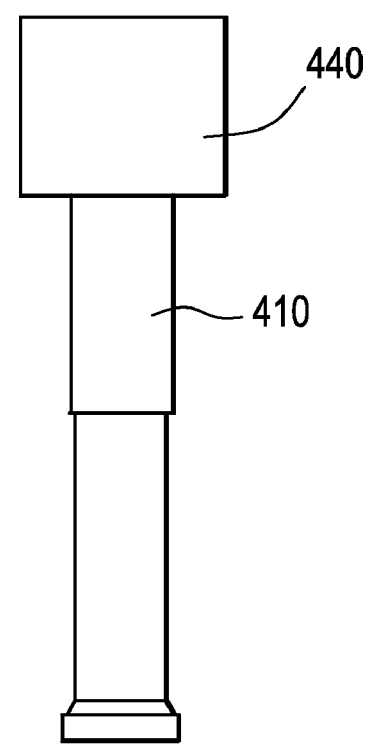

The column 410 is extendable in the longitudinal direction. It is continuously extendable from the shortest state shown in FIG. 2 to the longest state shown in FIG. 3 under the control of the operator console 600. In FIGS. 2 and 3, (a) is a side view and (b) is a front view.

Figure 4:
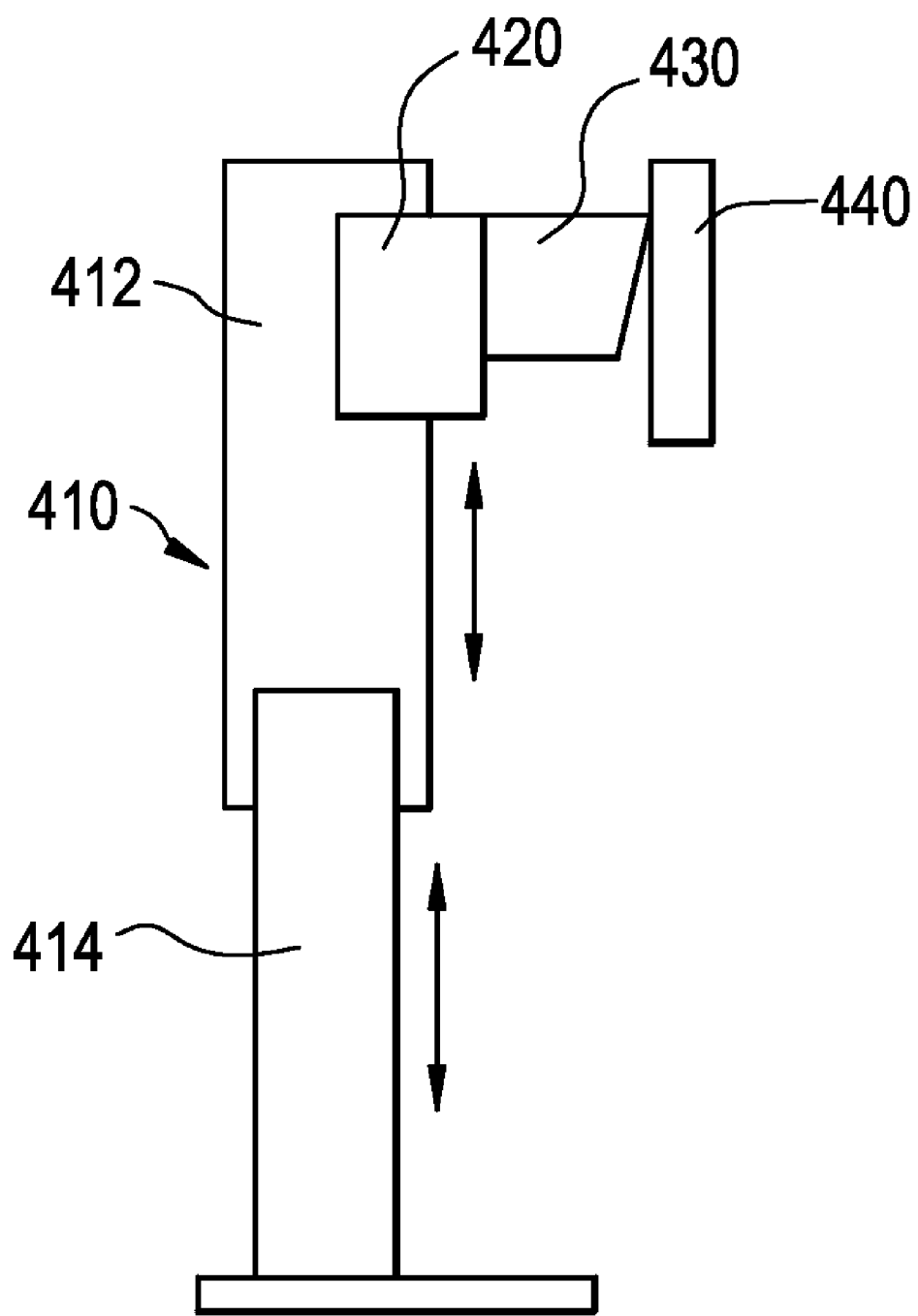
FIG. 4 is a view showing a structure of an X-ray detecting apparatus according to one example of a best mode for carrying out the present invention.

The column 410 is composed of an upper column 412 and a lower column 414 as shown in FIG. 4. The upper column 412 is telescopically engaged with the lower column 414. The lower column 414 is one example of a first column according to the present invention. The upper column 412 is one example of a second column according to the present invention. With this configuration, the column 410 is telescopically extendable.

The carriage 420 is disposed to the upper column 412 so as to be movable in the lengthwise direction. The movable distance of the carriage 420 on the upper column 412 is, for example, 830 mm. The movable distance of the upper column on the lower column 414 is, for example, 670 mm. Accordingly, the total movable distance of the carriage is 1500 mm. The length of the column 410 is, for example, 1370 mm minimum and 2040 mm maximum corresponding to the movable distance of the carriage 420.

Even if the X-ray irradiating device 200 is arranged such that its column 210 is coaxial with the column 410 of the X-ray detecting apparatus 400, both devices do not interfere with each other, since the length of the column 410 is extendable/retractable as described above. The column 410 is extended when the column 210 is shortened for raising the position of the X-ray source 220. Therefore, both devices do not interfere with each other.

Since the column 210 and the column 410 may be coaxially arranged, the length of the arm 430 supporting the X-ray detector 440 can be shortened, with the result that the stability of supporting the X-ray detector 440 can be enhanced. The column 410 and the arm 430 are both shortened, so that the X-ray detecting apparatus is downsized, which is convenient for packing, transportation, installation, or the like.

Figure 5A:
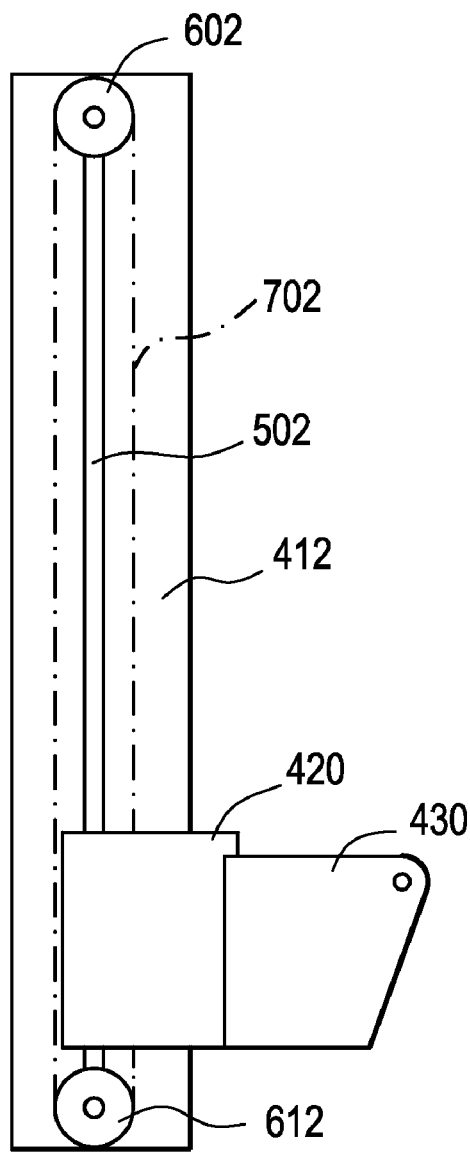
FIGS. 5a and 5b are views showing a structure of a carriage raising/lowering mechanism in an X-ray detecting apparatus according to one example of a best mode for carrying out the present invention.
Figure 5B:
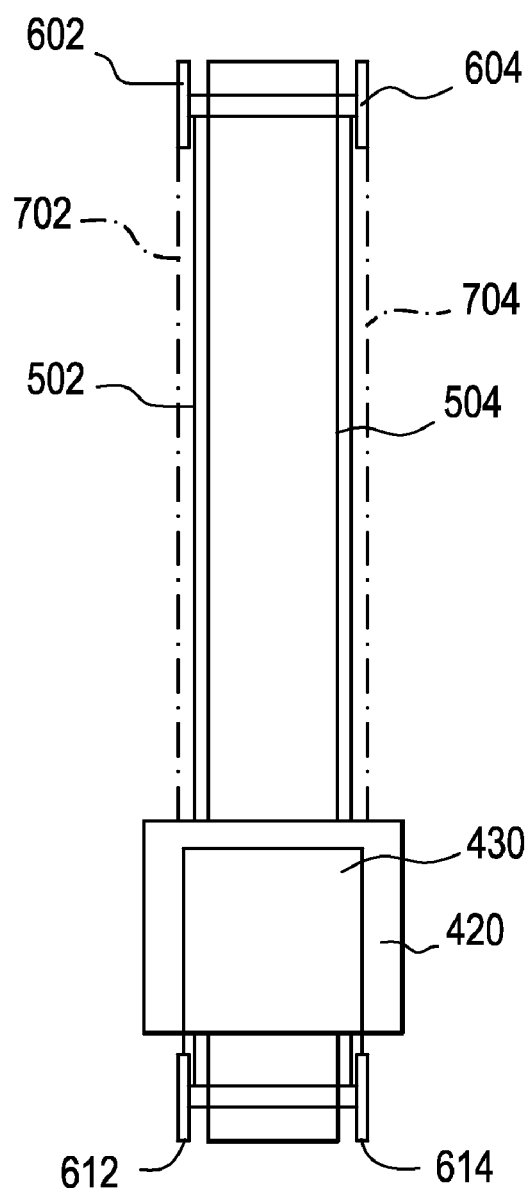
Figure 7:
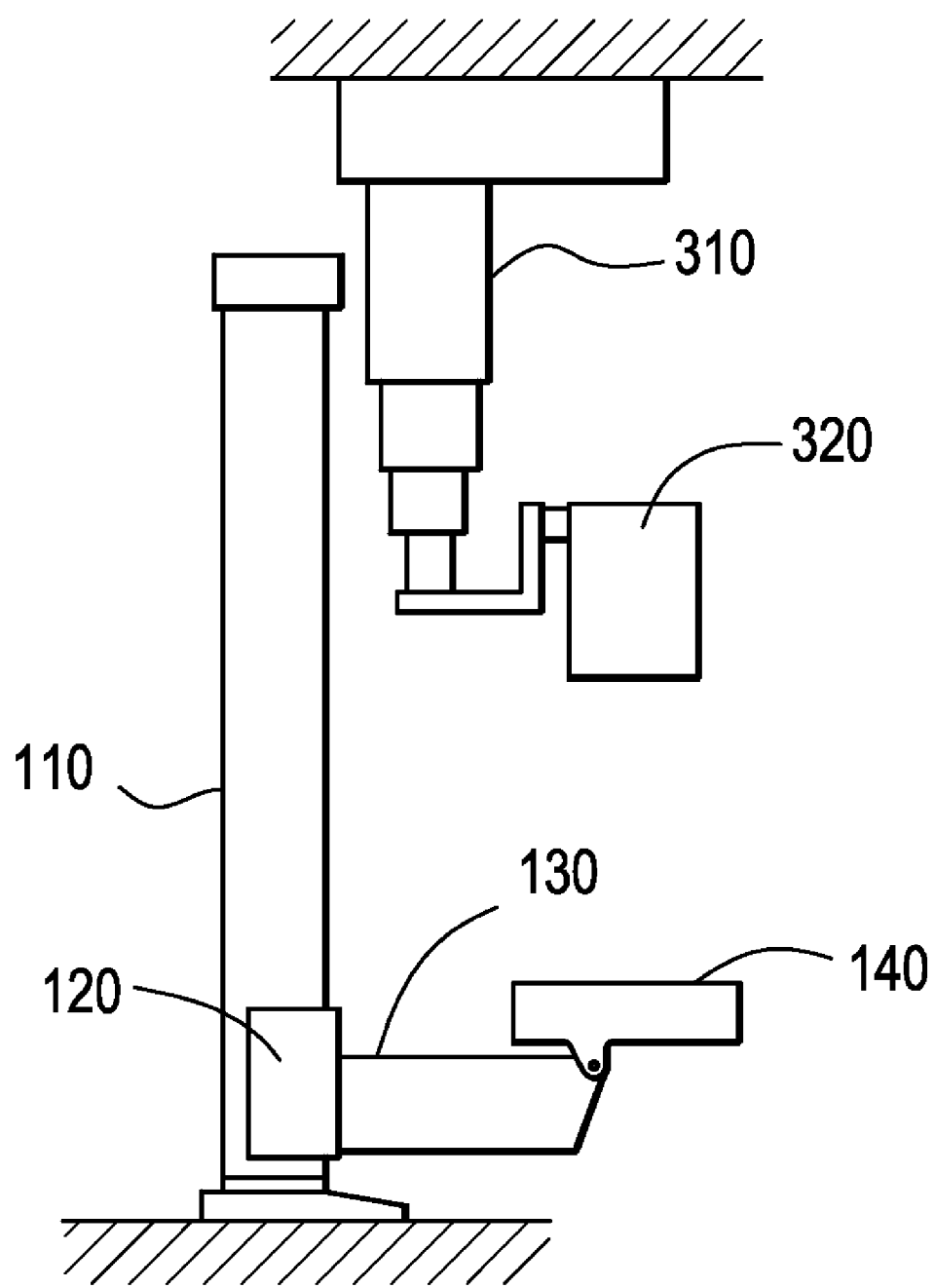
FIG. 7 is a view showing a structure of a conventional X-ray imaging apparatus.

Subsequently, a raising/lowering mechanism of the carriage 420 and extension mechanism of the column 410 will be explained. FIG. 5 show views of a structure of the carriage raising/lowering mechanism. In FIG. 5, (a) is a side view, while (b) is a front view. The carriage raising/lowering mechanism is one example of a second raising/lowering mechanism according to the present invention.

As shown in FIG. 5, the carriage raising/lowering mechanism has a pair of guide rails 502 and 504. The guide rails 502 and 504 are attached to both side faces of the upper column 412 so as to be parallel to the shaft. The carriage 420 has inside thereof a slider and roller engaged with these guide rails 502 and 504. The carriage 420 is movable along the guide rails 502 and 504.

A pair of drive gears 602 and 604 and a pair of driven gears 612 and 614 are provided at both side faces of both edge sections of the upper column 412 for moving the carriage 420. Chains 702 and 704 are entrained about the drive gear 602 and the driven gear 612 and about the drive gear 604 and the driven gear 614. A part of the respective chains 702 and 704 is fixed to the carriage 420.

Therefore, when the drive gears 602 and 604 rotate in the normal direction and reverse direction as driven by a motor incorporated in the upper column 412, the carriage 420 moves up and down along the guide rails 502 and 504 with the rotations.

The guide rails 502 and 504 function as a linear guide. The linear guide is one example of a linear guide according to the present invention. The carriage raising/lowering mechanism has the linear guide, whereby meandering of the carriage 420 during the upward and downward movements can be prevented.

The portion composed of the drive gears 602 and 604, driven gears 612 and 614 and chains 702 and 704 is one example of a combination of gear and chain according to the present invention. The carriage raising/lowering mechanism has the combination of gear and chain, whereby raising and lowering the X-ray detector can be easily performed. Note that raising and lowering the carriage 420 is performed not only by the combination of gear and chain but also by a suitable mechanism such as a combination of gear and toothed belt.

FIG. 6 show views of a structure of a column extension mechanism. In FIG. 6, (a) is a longitudinal sectional view seen from a side, while (b) is a front view. The column extension mechanism is one example of a first raising/lowering mechanism according to the present invention.

As shown in FIG. 6, the lower column 414 has a pair of guide rails 802 and 804. The guide rails 802 and 804 are attached to the front and back surfaces of the lower column 414 so as to be parallel to the shaft. The upper column 412 has inside thereof a slider and roller engaged with the guide rails 802 and 804, and is movable along the guide rails 802 and 804.

A linear actuator 902 is provided in the lower column 414 so as to be parallel to the shaft for moving the upper column 412. A gas spring 904 is provided parallel to the shaft in the lower column 414.

The working edges of the linear actuator 902 and the gas spring 904 are connected to the upper end section of the upper column 412 at the inside thereof. The linear actuator 902 pushes up or pulls down the upper column 412. The gas spring 904 generates force against the weight of the upper column 412 for reducing the load of the linear actuator 902.

The upper column 412 is driven by the linear actuator 902, so that it moves up and down the lower column 414 along the guide rails 802 and 804. Accordingly, the column 410 is telescopically extended/retracted.

The combination of the linear actuator 902 and the gas spring 904 is one example of a combination of linear actuator and gas spring according to the present invention. The guide rails 802 and 804 are one example of a linear guide according to the present invention.

The column extension mechanism has the combination of linear actuator and gas spring, so that the column can easily be extended and retracted. Further, it has the linear guide, whereby meandering of the column upon the extension/retraction can be prevented. Note that the upper column 412 is moved up and down by not only the combination of linear actuator and gas spring but also by a suitable mechanism such as a liner motor or the like.

The height (absolute height) of the X-ray detector 440 from the floor is changed with the movement of the upper column 412 on the lower column 414 and the movement of the carriage 420 on the upper column 412. An encoder 910 is provided at the base section of the lower column 414 in order to detect the absolute height of the X-ray detector 440. The rotator of the encoder 910 is coupled to the carriage 420 via a non-expansion wire, not illustrated, whose extension and reel-up are possible.

The height detection signal of the encoder 910 is inputted to the operator console 600. Thus, the operator console 600 can recognize the absolute height of the X-ray detector 440. The encoder 901 is one example of an encoder according to the present invention.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray detecting apparatus comprising:
a vertical first column;
a second column that is telescopically engaged with the first column;
a first raising/lowering mechanism that moves up/down the second column along the first column;
a carriage attached to the second column;
a second raising/lowering mechanism that moves up/down the carriage along the second column; and
an X-ray detector held by an arm extending horizontally from the carriage.

2. An X-ray detecting apparatus according to claim 1, wherein
the first column has a linear guide for the second column.

3. An X-ray detecting apparatus according to claim 2, wherein
the first raising/lowering mechanism has a combination of a linear actuator and a gas spring.

4. An X-ray detecting apparatus according to claim 3, wherein
the second column has a linear guide for the carriage.

5. An X-ray detecting apparatus according to claim 3, wherein
the second raising/lowering mechanism has a combination of a gear and a chain.

6. An X-ray detecting apparatus according to claim 2, wherein
the second column has a linear guide for the carriage.

7. An X-ray detecting apparatus according to claim 2, wherein
the second raising/lowering mechanism has a combination of a gear and a chain.

8. An X-ray detecting apparatus according to claim 1, wherein
the first raising/lowering mechanism has a combination of a linear actuator and a gas spring.

9. An X-ray detecting apparatus according to claim 8, wherein
the second column has a linear guide for the carriage.

10. An X-ray detecting apparatus according to claim 8, wherein
the second raising/lowering mechanism has a combination of a gear and a chain.

11. An X-ray detecting apparatus according to claim 1, wherein
the second column has a linear guide for the carriage.

12. An X-ray detecting apparatus according to claim 11, wherein
the second raising/lowering mechanism has a combination of a gear and a chain.

13. An X-ray detecting apparatus according to claim 1, wherein
the second raising/lowering mechanism has a combination of a gear and a chain.

14. An X-ray detecting apparatus according to claim 1, wherein
the first column has an encoder for detecting the absolute height of the X-ray detector.

15. An X-ray imaging apparatus having an X-ray irradiating device and an X-ray detecting apparatus opposing to the X-ray irradiating device,
the X-ray detecting apparatus comprising:
a vertical first column;
a second column that is telescopically engaged with the first column;
a first raising/lowering mechanism that moves up/down the second column along the first column;
a carriage attached to the second column;
a second raising/lowering mechanism that moves up/down the carriage along the second column; and
an X-ray detector held by an arm extending horizontally from the carriage.

16. An X-ray imaging apparatus according to claim 15, wherein the first column has a linear guide for the second column.

17. An X-ray imaging apparatus according to claim 15, wherein
the first raising/lowering mechanism has a combination of a linear actuator and a gas spring.

18. An X-ray imaging apparatus according to claim 15, wherein
the second column has a linear guide for the carriage.

19. An X-ray imaging apparatus according to claim 15, wherein
the second raising/lowering mechanism has a combination of a gear and a chain.

20. An X-ray imaging apparatus according to claim 15, wherein
the first column has an encoder for detecting the absolute height of the X-ray detector.

* * * * *